(12) United States Patent
Momozawa et al.

(10) Patent No.: US 10,412,958 B2
(45) Date of Patent: Sep. 17, 2019

(54) DEVICE FOR CELL OR TISSUE CRYOPRESERVATION BY VITRIFICATION

(71) Applicants: SCHOOL JURIDICAL PERSON KITASATO INSTITUTE, Minato-ku, Tokyo (JP); MITSUBISHI PAPER MILLS LIMITED, Sumida-ku, Tokyo (JP)

(72) Inventors: Kenji Momozawa, Sagamihara (JP); Atsushi Matsuzawa, Sumida-ku (JP); Katsumitsu Susaki, Sumida-ku (JP)

(73) Assignees: SCHOOL JURIDICAL PERSON KITASATO INSTITUTE, Tokyo (JP); MITSUBISHI PAPER MILLS LIMITED, Tokyo (JP)

( * ) Notice: Subject to any disclaimer, the term of this patent is extended or adjusted under 35 U.S.C. 154(b) by 97 days.

(21) Appl. No.: 15/025,571

(22) PCT Filed: Oct. 17, 2014

(86) PCT No.: PCT/JP2014/077646
§ 371 (c)(1),
(2) Date: Mar. 29, 2016

(87) PCT Pub. No.: WO2015/064380
PCT Pub. Date: May 7, 2015

(65) Prior Publication Data
US 2016/0235056 A1 Aug. 18, 2016

(30) Foreign Application Priority Data

Oct. 29, 2013 (JP) ................................ 2013-223894
May 7, 2014 (JP) ................................ 2014-095891

(51) Int. Cl.
*C12M 3/00* (2006.01)
*A01N 1/00* (2006.01)
(Continued)

(52) U.S. Cl.
CPC ........... *A01N 1/0268* (2013.01); *C12M 45/22* (2013.01)

(58) Field of Classification Search
CPC ......... C12M 21/08; C12M 25/02; A01N 1/02; A01N 1/0236; A01N 1/0242
See application file for complete search history.

(56) References Cited

U.S. PATENT DOCUMENTS 5,272,081 A * 12/1993 Weinreb ................. C12M 23/12
435/243
5,780,295 A 7/1998 Livesey et al.
(Continued)

FOREIGN PATENT DOCUMENTS

CN 101111603 1/2008
CN 103179852 6/2013
(Continued)

OTHER PUBLICATIONS

English translation of Fukuda (JP 2005-040073) (Feb. 17, 2005).*
(Continued)

*Primary Examiner* — Nathan A Bowers
(74) *Attorney, Agent, or Firm* — Venable LLP

(57) ABSTRACT

Provided is a device for vitrification-based cryopreservation which enables easy and reliable vitrification freezing of cells or tissues. The device of the present invention for cell or tissue cryopreservation by vitrification has a porous structure made of a material having a refractive index of 1.45 or less as a vitrification solution absorber.

6 Claims, 1 Drawing Sheet

(51) Int. Cl.
*A01N 1/02* (2006.01)
*C12M 1/00* (2006.01)

(56) References Cited

U.S. PATENT DOCUMENTS

| | | | |
|---|---|---|---|
| 5,965,438 A | 10/1999 | Kadkade et al. | |
| 2010/0003662 A1* | 1/2010 | Kagawa | A01N 1/0242 435/1.3 |
| 2010/0297675 A1 | 11/2010 | Deng et al. | |
| 2013/0137080 A1 | 5/2013 | Henderson et al. | |

FOREIGN PATENT DOCUMENTS

| | | |
|---|---|---|
| EP | 0 757 139 | 2/1997 |
| JP | 62-117603 | 5/1987 |
| JP | 8-218567 | 8/1996 |
| JP | 10-248860 | 9/1998 |
| JP | 3044323 | 3/2000 |
| JP | 2002-315573 | 10/2002 |
| JP | 2005-040073 | 2/2005 |
| JP | 2006-271395 | 10/2006 |
| JP | 2007-124971 | 5/2007 |
| JP | 2008-005846 | 1/2008 |
| JP | 2008-136908 | 6/2008 |
| JP | 2010-068755 | 4/2010 |
| JP | 2012-509960 | 4/2012 |
| WO | 2006/058286 | 6/2006 |
| WO | 2009/105813 | 9/2009 |
| WO | 2011/070973 | 6/2011 |
| WO | 2012120514 | 9/2012 |
| WO | 2013020032 | 2/2013 |
| WO | 2013/098825 | 7/2013 |

OTHER PUBLICATIONS

Meeting Summary, Japanese Society of Animal Science (2010) 112th, 88, VI129-17.
Encyclopedia of Chemistry 1, Kyoritsu Shuppan Co., Ltd. (1960) 908.
Encyclopedia of Chemistry 4, Kyoritsu Shuppan Co., Ltd. (1960) 522.
Encyclopedia of Chemistry 3, Kyoritsu Shuppan Co., Ltd., (1960) 110-11.
URL, http://www.merckmillipore.com/JP/ja/product/%E3%83%87%E3%83%A5%E3%83.
Sakai, "Cryopreservation of Cultured Plant Cells and Meristems by Vitrification", Cryobiology and Cryotechnology, vol. 42, No. 1 (1996) 61-8.
Steponkus, et al., "Cryopreservation of *Drosophila melanogaster* embryos", Nature, vol. 345 (1990) 170-72.
Shuxin et al., "Experiment 31 Measurement of Polymer Birefringence", Polymer Science Experiment (2008).

* cited by examiner

DEVICE FOR CELL OR TISSUE CRYOPRESERVATION BY VITRIFICATION

TECHNICAL FIELD

The present invention relates to a device for vitrification-based cryopreservation designed to be used for freezing and preserving biological cells or tissues etc.

BACKGROUND ART

Highly efficient preservation techniques for biological cells or tissues are desired in various fields of industry. For example, in bovine embryo transfer technology, embryos need to be transferred in consideration of the estrus cycle of a recipient cow, and to this end, embryos cryopreserved in advance are thawed and transferred during a suitable phase of the estrus cycle. In human fertility treatment, eggs or ovaries harvested from a woman's body are cryopreserved until an appropriate timing for implantation, and the cryopreserved eggs are thawed before use in implantation.

In general, cells or tissues harvested from living bodies gradually become inactive even when they are in culture medium, and hence their long-term in vitro culture is undesirable. For this reason, techniques for long-term preservation of biological samples without the loss of biological activity are essential. Highly efficient preservation techniques would enable more accurate analysis of cells or tissues harvested from living bodies. Such preservation techniques would enable implantation of biological samples with their biological activity kept at a higher level, thus resulting in an improvement in the engraftment rate. It would be also possible that artificial tissues for implantation such as in vitro cultured skin or so-called cell sheet formed in vitro are produced in advance and stored until needed. Therefore, highly efficient preservation techniques are widely demanded in industry as well as in medical science.

One of the known methods for preserving cells or tissues is slow freezing, for example. In this method, cells or tissues are immersed in a preservation solution prepared by adding a cryoprotectant to a physiological solution such as phosphate buffered saline. Compounds used as the cryoprotectant include glycerol and ethylene glycol. The cells or tissues immersed in the preservation solution are cooled down to −30 to −35° C. at a relatively slow cooling rate (for example, 0.3 to 0.5° C./min.), and thereby the fluid inside the cells or tissues and the solution outside the cells or tissues are sufficiently cooled and become viscous. Further cooling down the cells or tissues in such a state in the preservation solution to the temperature of liquid nitrogen (−196° C.) allows both the inside of the cells or tissues and the closely surrounding solution to become amorphous solid, that is, vitrify. The vitrification (that is, solidification) inside and outside the cells or tissues arrests substantial molecular movement. Thus, the vitrified cells or tissues can be semi-permanently preserved in liquid nitrogen.

However, the slow freezing method requires relatively slow-rate cooling, and thus prolongs the process of cryopreservation. In addition, this method disadvantageously needs the use of a temperature controlling instrument or device. Furthermore, the slow freezing method cannot avoid ice crystal formation in the preservation solution outside the cells or tissues, which can cause physical damage to the cells or tissues.

A proposed solution to the problems of the slow freezing method is vitrification-based preservation. The vitrification-based preservation uses a principle that the addition of a large amount of a cryoprotectant, such as glycerol, ethylene glycol and DMSO (dimethyl sulfoxide), to water decreases the freezing point of water, thus preventing ice crystal formation at sub-zero temperatures. Such a cryoprotectant-containing aqueous solution solidifies without ice crystal formation when rapidly cooled in liquid nitrogen. This solidification is called vitrification freezing. The aqueous solution containing a large amount of a cryoprotectant is called a vitrification solution.

The specific procedure of the vitrification-based preservation is to immerse cells or tissues in a vitrification solution and to cool them at the temperature of liquid nitrogen (−196° C.). Such a simple and quick process of cryopreservation can be completed in less time without the use of any temperature controlling instrument or device.

The vitrification-based preservation does not cause ice crystal formation either inside or outside the cells, and thus can prevent physical damage (freezing damage) to the cells at the time of freezing and thawing. However, the high concentration of the cryoprotectant contained in the vitrification solution is chemically toxic, and therefore, the volume of the vitrification solution used in the cryopreservation process is preferably not more than necessary. In addition, the duration of exposure of the cells or tissues to the vitrification solution, that is, the time to freezing is preferably short. Furthermore, the vitrification solution should be diluted quickly and immediately after thawing.

The vitrification-based cryopreservation of cells or tissues as described above has been reported, and various examples using different methods and different kinds of cells and tissues have been presented. For example, Patent Literature 1 describes that the application of vitrification-based preservation to reproductive or somatic cells of animal or human origin is very useful in terms of the cell viability after cryopreservation and thawing.

The vitrification-based preservation is a technique which has been developed mainly using human reproductive cells, and more recently, its application to iPS or ES cells has been widely examined. Non Patent Literature 1 describes the effectiveness of vitrification-based preservation of *Drosophila* embryos. Patent Literature 2 and Non Patent Literature 2 describe the effectiveness of vitrification-based preservation of plant culture cells and tissues. As just described, vitrification-based preservation is known to be useful for a wide range and different kinds of cells and tissues.

The devices and procedures for more efficient vitrification-based preservation have been reported in publications. For example, Patent Literature 3 reports an attempt to improve the recovery rate of eggs or embryos cryopreserved by vitrification in a straw. The procedure includes vitrifying and preserving eggs or embryos in a claimed straw filled with a vitrification solution, and bringing the cryopreserved eggs or embryos into contact with a diluent in the straw quickly and immediately after thawing.

Patent Literature 4 proposes a cryopreservation method comprising placing eggs or embryos with a vitrification solution on a vitrification solution-removing material and removing excess vitrification solution surrounding the eggs or embryos by downward suction through the vitrification solution-removing material. The eggs or embryos cryopreserved by this method are shown to retain high viability. Examples of the vitrification solution-removing material described in the literature include wire mesh and perforated films made of natural substances, such as paper, or synthetic resins.

Patent Literature 5 proposes a cryopreservation method comprising absorbing excess vitrification solution surrounding eggs or embryos with an absorber such as a filter paper. The eggs or embryos cryopreserved by this method are shown to retain high viability.

Patent Literature 6 and Patent Literature 7 propose the so-called Cryotop method, which is used in the field of fertility treatment in humans. This cryopreservation method uses a flexible, clear and colorless film strip as an egg holding strip and comprises depositing eggs or embryos with a very small amount of a vitrification solution on the film under a microscope.

CITATION LIST

Patent Literature

Patent Literature 1: Japanese Patent No. 3044323
Patent Literature 2: JP-A 2008-5846
Patent Literature 3: JP-A 10-248860
Patent Literature 4: WO 2011/070973
Patent Literature 5: JP-A 2005-40073
Patent Literature 6: JP-A 2002-315573
Patent Literature 7: JP-A 2006-271395

Non Patent Literature

Non Patent Literature 1:
Steponkus et al., Nature 345: 170-172 (1990)
Non Patent Literature 2:
Akira Sakai, Japanese Society for Cryobiology and Cryotechnology 42: 61-68 (1996)

SUMMARY OF INVENTION

Technical Problem

The method proposed in Patent Literature 3 involves filling up a straw with a vitrification solution, resulting in a prolonged time to freeze the vitrification solution. In addition, the size of cells or tissues to be cryopreserved is limited by the inner diameter of the straw, and a sheet-like tissue such as cell sheet is difficult to preserve in the straw.

The method proposed in Patent Literature 4 for cryopreservation of reproductive cells involves removing excess vitrification solution surrounding eggs or embryos to ensure their high viability. However, the removal of excess vitrification solution in this method requires downward suction, which is a cumbersome step. Therefore, this method is unsuitable for quick completion of vitrification-based cryopreservation. Another problem is that excess vitrification solution may remain around the eggs or embryos when the downward suction is insufficient.

The method proposed in Patent Literature 5 for cryopreservation of reproductive cells involves absorbing excess vitrification solution surrounding eggs or embryos with an absorber such as filter paper to ensure their high viability. In the case where vitrification-based preservation is applied to, for example, human eggs or embryos according to the Cryotop method, the deposition of the eggs or embryos on the absorber must be checked with a high level of reliability. However, since the total light transmittance of filter paper is low, it is difficult to observe the eggs or embryos deposited on filter paper under a commonly used transmission optical microscope. Therefore, it is almost impossible to check the deposition of eggs or embryos in a reliable manner. Another problem is that when the cryopreserved eggs or embryos are thawed, they are difficult to retrieve from the absorber without fail.

The methods proposed in Patent Literature 6 and Patent Literature 7 solve the problems of the method proposed in Patent Literature 5 to some extent. The method proposed in Patent Literature 6 or Patent Literature 7 provides a device for egg cryopreservation which is user-friendly and compact so as to occupy less space for storage. The device for egg cryopreservation has a flexible, clear and colorless flat film (egg holding strip) on which human eggs or embryos can be observed under a microscope. In the process of cryopreservation of eggs or embryos, eggs or embryos with a very small amount (0.1 µL) of a vitrification solution are deposited dropwise on the film. However, considerable skill is required to accurately deposit dropwise a very small amount of an egg- or embryo-containing vitrification solution on the film of usually 0.5 to 2 mm in width. In fact, the first hurdle for many inexperienced culture technicians in the procedure of freezing eggs or embryos is to place eggs or embryos with a very small amount of fluid on the sheet. When the amount of the vitrification solution placed dropwise is relatively larger, excess vitrification solution remains around the eggs or embryos and can reduce the viability of the eggs or embryos due to its toxicity. Therefore, methods for solving the difficulty and complicatedness of the above procedure are desired.

The main object of the present invention is to provide a device for vitrification-based cryopreservation which enables easy and reliable cryopreservation of cells or tissues. The object is, more specifically, to provide a device for vitrification-based cryopreservation designed for good absorption performance in absorbing excess vitrification solution on a vitrification solution absorber upon dropwise placement of a cell or tissue immersed in a vitrification solution, and for good visibility (reliable checking for the deposition of the cell or tissue) in the observation of the cell or tissue on the vitrification solution absorber under a transmission optical microscope. Another object of the present invention is to provide a device for vitrification-based cryopreservation designed for good absorption performance in absorbing excess vitrification solution and for good visibility in the observation of the cell or tissue placed on the cryopreservation device in the thawing procedure after cryopreservation.

Solution to Problem

As a result of intensive research, the present inventors found that the above-mentioned technical objects can be achieved by a device which is used for cell or tissue cryopreservation by vitrification and has the following constitution.

(1) A device for cell or tissue cryopreservation by vitrification, the device having a porous structure made of a material having a refractive index of 1.45 or less as a vitrification solution absorber.
(2) The device according to the above (1), wherein the pore size of the porous structure is 5.5 µm or less.
(3) The device according to the above (2), wherein the porous structure is made of fluororesin.

Advantageous Effects of Invention

The present invention provides a device for cell or tissue cryopreservation by vitrification which enables easy and simple cryopreservation of cells or tissues. That is, according to the present invention, after a cell or tissue immersed in a vitrification solution is placed on a vitrification solution absorber of the cryopreservation device, the absorber absorbs excess vitrification solution surrounding the cell or tissue, thus eliminating the need to do extra operations for removing the excess vitrification solution (for example, downward suction through the vitrification solution absorber, or direct suction into a micropipette etc. from the periphery of the cell or tissue).

In addition, after a vitrification solution containing cells or tissues is placed dropwise on the vitrification solution absorber of the cryopreservation device of the present invention, the cell or tissue placed on the absorber can easily be observed under an optical microscope. Therefore, the device of the present invention for vitrification-based cryopreservation enables easy, reliable and efficient vitrification freezing of cells or tissues. Furthermore, the cell or tissue placed on the device of the present invention for vitrification-based cryopreservation can be observed with good visibility in the thawing procedure. Therefore, the device of the present invention for vitrification-based cryopreservation enables easy, reliable and efficient thawing of the frozen cells or tissues.

DESCRIPTION OF EMBODIMENTS

Figure 1:
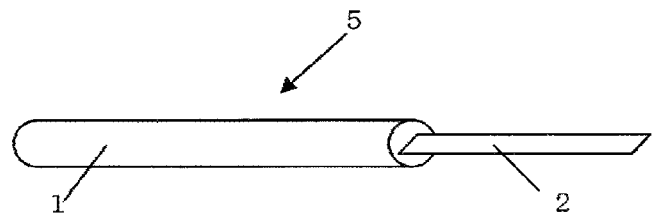
FIG. 1 is a perspective view showing an example of the device of the present invention for cell or tissue cryopreservation by vitrification.

Hereinafter, the "device for cell or tissue cryopreservation by vitrification" of the present invention will be described in detail, but the present invention is not limited to the following embodiments. The "device for cell or tissue cryopreservation by vitrification" of the present invention has a porous structure made of a material having a refractive index of 1.45 or less as a vitrification solution absorber.

The device of the present invention for vitrification-based cryopreservation is used for cryopreservation of a cell or tissue of a living organism. The cell as used herein encompasses not only a single cell but also a cell population composed of a plurality of cells. The cell population composed of a plurality of cells may be a cell population composed of cells of a single kind, or a cell population composed of cells of a plurality of kinds. The tissue may be composed of cells of a single kind, or composed of cells of a plurality of kinds. Moreover, the tissue may contain a noncellular substance like extracellular matrix in addition to the cells. The device of the present invention for vitrification-based cryopreservation is designed to be preferably used for freezing a cell or tissue as follows. A cell or tissue with a vitrification solution is deposited on the vitrification solution absorber of the cryopreservation device of the present invention, and the vitrification solution absorber holding the cell or tissue is then immersed in a coolant, such as liquid nitrogen. The vitrification solution absorber of the cryopreservation device of the present invention facilitates the holding of the cell or tissue with a vitrification solution and the immersion of the cell or tissue in liquid nitrogen. The device of the present invention for vitrification-based cryopreservation can be put in another way as a tool for cell or tissue cryopreservation, or as a tool for cell or tissue preservation by vitrification.

The device of the present invention for vitrification-based cryopreservation ensures a very high viability of a cell or tissue even when a cell or tissue immersed in a vitrification solution is placed dropwise, with a relatively large amount of the solution, on the vitrification solution absorber of the cryopreservation device of the present invention. This is because the absorber absorbs excess vitrification solution surrounding the cell or tissue. Furthermore, the cell or tissue which has been subjected to the above operation is covered with a very small amount of the vitrification solution, and thus can be quickly frozen during the freezing procedure. Such a very small amount of the vitrification solution can be diluted quickly and immediately after the cryopreserved cell or tissue is thawed.

The device of the present invention for vitrification-based cryopreservation at least has a vitrification solution absorber, i.e. a part capable of absorbing a vitrification solution, and the vitrification solution absorber is a porous structure made of a material having a refractive index of 1.45 or less. Preferably, the refractive index of the material is 1.39 or less but 1.30 or more so that the cell or tissue on the vitrification solution absorber can be easily observed under a microscope. The refractive index of the material of the porous structure serving as the vitrification solution absorber can be measured with an Abbe refractometer (sodium light source, wavelength: 589 nm) according to JIS K0062 or JIS K7142. The porous structure in the present invention is a structure having pores on the surface, and preferably a structure having continuous pores on the surface and the inside. The vitrification solution absorber of the present invention may have only the above-described porous structure without any support. Alternatively, the vitrification solution absorber may have a support and the above-described porous structure as a vitrification solution absorbing layer on the support. In the case where a vitrification solution absorbing layer is provided on a support, an adhesive layer can be provided between the support and the vitrification solution absorbing layer. In addition to the vitrification solution absorbing layer and the adhesive layer, for example, an undercoat layer etc. can be provided on the support in order that an even and uniform adhesive layer can be formed.

After a vitrification solution containing a cell or a tissue is placed dropwise on the vitrification solution absorber of the device of the present invention for vitrification-based cryopreservation, the vitrification solution is promptly absorbed into the vitrification solution absorber through the pores on the surface of the porous structure, and thereby excess vitrification solution surrounding the cell or tissue can be removed. When the pores of the porous structure are filled with the vitrification solution placed dropwise and absorbed thereinto, the transparency of the vitrification solution absorber is increased because the difference between the refractive indexes of the vitrification solution absorber and the vitrification solution is small (the refractive index of the vitrification solution is generally 1.43 to 1.33). Thus, the cell or tissue deposited on the vitrification solution absorber can easily be observed under a transmission optical microscope. In particular, in the case where the cell to be cryopreserved is an egg and/or embryo of human or mouse origin, the method of Patent Literature 6 or 7 has difficulty in visually confirming the egg in a vitrification solution, but according to the present invention, the absorption of excess vitrification solution by the vitrification solution absorber of the device for vitrification-based cryopreservation makes it easier to visually confirm the egg.

Preferable examples of the form of the vitrification solution absorber of the present invention include a porous structure in the form of a porous membrane produced by stretching; a porous structure made of fiber; a porous structure having a three-dimensional lattice (mesh) structure; a porous structure formed by sintering a powder material etc.; and a porous medium in the form of a porous membrane produced by phase separation.

The porous structure can be produced by reference to known production methods including the following:

the method described in JP-A 42-13560, that is, "a method for producing a porous structure material, comprising shaping a body from an unsintered polytetrafluoroethylene mixture containing a liquid lubricant by extrusion and/or rolling, and stretching the shaped body in at least one direction in an unsintered state, followed by heating it to about 327° C. or more";

the method described in JP-A 2010-94579, that is, "a method for producing a porous fluororesin film, comprising fixing, to a support capable of being extended by stretching, a fluororesin film which is composed of a fluororesin mixture mainly containing polytetrafluoroethylene and has a thickness of 50 μm or less, and stretching the resulting body at less than 30° C. to form a porous structure";

the method described in JP-A 2012-97363, that is, "a method for producing a non-woven fabric, comprising applying a voltage between an electrode for charging fluororesin at least partly in a molten state, and a collector arranged to face the charging electrode, thereby making the molten fluororesin into fibers; and collecting the fibers on the collector, the method being characterized that the charging electrode is used as a negative electrode while applying a voltage";

the method described in JP-A 2011-245854, that is, "a method for producing a honeycomb structure having a ceramic block and a coat layer in the periphery of the ceramic block, the ceramic block being composed of fired columnar honeycomb bodies joined via an adhesive layer, the fired columnar honeycomb bodies having a large number of cells that are arranged in parallel in a longitudinal direction and separated by cell walls, the method comprising the steps:

forming a honeycomb body having a cell wall in the outer periphery by extrusion, firing the honeycomb body to give a fired honeycomb body, fixing a plurality of the fired honeycomb bodies in a mold, injecting a sealing paste into a gap between the mold and the fired honeycomb bodies and into a gap between the fired honeycomb bodies, and drying and solidifying the sealing paste to form an adhesive layer and a coat layer, the method being characterized in that the sealing paste contains a particulate inorganic material and/or an inorganic fiber, that the mold, the inside of the mold, or a member disposed at the inner side of the mold is provided with a ventilation part through which air flows, and that the drying step involves drying and solidifying the sealing paste in contact with at least part of the ventilation part";

the method described in JP-A 2007-46042, that is, "a method for producing a porous structure using a reversed micelle template formed in a hydrophobic organic solvent solution for formation of pores, the method comprising the steps:

preparing a hydrophobic organic solvent solution in which a reversed micelle is formed by stirring a solution at least containing an amphipathic substance, a hydrophobic organic polymer, a hydrophilic liquid and a hydrophobic organic solvent for dissolving the organic polymer;

casting the hydrophobic organic solvent solution on a substrate; and evaporating the hydrophobic organic solvent and the hydrophilic liquid from the hydrophobic organic solvent solution on the substrate to form a porous structure"; and the like.

Examples of the material that has a refractive index of 1.45 or less and can be processed into the above-mentioned porous structure include plastic resin materials such as silicone resins and fluororesins including polytetrafluoroethylene, polyvinylidenedifluoride and polychlorotrifluoroethylene; metal oxide materials such as silicon dioxide; and inorganic materials such as sodium fluoride, magnesium fluoride and calcium fluoride. Other examples include polymeric materials having a refractive index controlled by the method described in JP-A 2000-95862, and the materials that are described in JP-A 2007-279459 and made of a polymer alloy containing a mixture of two or more kinds of polymers. Preferred is a porous structure made of fluororesin, more preferred are polytetrafluoroethylene and polyvinylidenedifluoride, and particularly preferred is polytetrafluoroethylene. The porous structure may further contain a material other than the above-mentioned material. In this case, the material having a refractive index of 1.45 or less as mentioned above accounts for preferably 85% by mass or more, and more preferably 90% by mass or more of the component materials of the porous structure.

The surface of the vitrification solution absorber of the present invention is preferably hydrophilized for the enhancement of the vitrification solution-absorbing performance. Examples of the hydrophilization method include graft modification; coating with a hydrophilic polymeric compound etc.; corona discharge treatment, plasma treatment and other common methods for surface modification using various electron beams such as excimer laser.

The pore size of the porous structure of the vitrification solution absorber of the present invention is preferably 0.02 to 20 μm, and more preferably 0.2 to 15 μm in consideration of the vitrification solution-absorbing capability and the visibility in checking for the deposition of the cell or tissue on the vitrification solution absorber (the visibility in transmission optical microscopy). In addition, the pore size of the porous structure of the vitrification solution absorber is preferably 5.5 μm or less, more preferably 1.0 μm or less, and still more preferably 0.75 μm or less in consideration of the vitrification solution-absorbing capability and the visibility of the cell or tissue placed on the vitrification solution absorber immersed in a thawing solution for the observation during thawing after cryopreservation.

When the pore size of the porous structure of the vitrification solution absorber is less than 0.02 μm, the absorption of the vitrification solution placed dropwise is insufficient. As a result, more time may be required before cryopreservation, or excess vitrification solution may remain around the cell or tissue. When the pore size exceeds 20 μm, the cell or tissue may be trapped in a pore on the surface. In that case, the cell or tissue may not be easily detachable from the vitrification solution absorber during thawing after freezing, and thus thawing may not be done properly. Furthermore, the cell or tissue deposited on the vitrification solution absorber may be hardly discernible from the pores on the surface of the vitrification solution absorber, and thus the visibility is unsatisfactory.

The thickness of the porous structure of the vitrification solution absorber according to the present invention is preferably 10 to 500 μm, and more preferably 25 to 150 μm. In addition, the porosity of the porous structure is preferably 30% or more, and more preferably 70% or more. The pore size, thickness and porosity of the porous structure of the vitrification solution absorber of the present invention can be determined as appropriate for the kind of the cell or tissue to be used, the amount of the vitrification solution placed dropwise with the cell or tissue, etc.

As used herein, the pore size of the porous structure is the diameter of the largest opening measured according to the method for bubble point testing specified in JIS K3832. The porosity is defined by the formula shown below.

The void volume V in the formula can be calculated as a value per unit area (m$^2$) by multiplying the cumulative pore volume (mL/g) by the dry solids content (g/m$^2$) of the vitrification solution absorber. The cumulative pore volume is the total volume of pores with a radius of 3 to 400 nm, and is determined by measurement and data analysis with a mercury porosimeter (measuring instrument name: Autopore II 9220, manufacturer: Micromeritics Instrument Corporation). The vitrification solution absorber thickness T can be determined by capturing an electron microscopic image of the cross section of the vitrification solution absorber and measuring the thickness of the cross section.

$$P=(V/T)\times 100(\%)$$

P: Porosity (%)
V: Void volume (mL/m$^2$)
T: Vitrification solution absorber thickness (μm)

The area of the vitrification solution absorber of the present invention can be determined as appropriate for the amount of the vitrification solution placed dropwise with the cell or tissue, etc. and is not particularly limited. For example, the area of the vitrification solution absorber is preferably 10 mm$^2$ or more, and more preferably 20 to 400 mm$^2$ per microliter of the vitrification solution placed dropwise.

In the case where the vitrification solution absorber of the device of the present invention for vitrification-based cryopreservation has a support, the support is preferably an optically transparent support, and more preferably an optically transparent support having a total light transmittance of 80% or more. The haze value of the optically transparent support is preferably 10% or less. Examples of the support having these properties include various kinds of resin films, glasses and rubbers. Two or more kinds of supports may be used in combination as long as the effects of the present invention can be achieved. In particular, resin films are preferably used because of their ease of handling. Specific examples of resin films include resin films made of polyester resin such as polyethylene terephthalate (PET) and polyethylene naphthalate (PEN), acrylic resin, epoxy resin, silicone resin, polycarbonate resin, diacetate resin, triacetate resin, polyarylate resin, polyvinyl chloride resin, polysulfone resin, polyether sulfone resin, polyimide resin, polyamide resin, polyolefin resin, cyclic polyolefin resin or the like. The thickness of resin films is preferably 10 to 1000 μm. The surface of the support can be subjected to an adhesion improving treatment using corona discharge to increase the adhesion strength between the support and the adhesive layer.

In the case where the vitrification solution absorber of the device of the present invention for vitrification-based cryopreservation has an adhesive layer, common adhesion methods using an instant adhesive (a typical example is a moisture-curable adhesive), a hot melt adhesive, a photo-curable adhesive, etc. can be employed. For example, preferable adhesives include water-soluble adhesives such as polyvinyl alcohol, hydroxycellulose, polyvinyl pyrrolidone and starch paste; and water-insoluble adhesives such as vinyl acetate adhesives, acrylic adhesives, epoxy adhesives, urethane adhesives, elastomer adhesives, cyanoacrylate adhesives, fluorine adhesives, silicone adhesives, nitrocellulose adhesives, nitrile rubber adhesives, styrene-butadiene adhesives, urea resin adhesives, styrene resin adhesives, phenolic resin adhesives, polyimide adhesives, polyamide adhesives, polyester adhesives, bismaleimide adhesives, olefin adhesives and EVA adhesives. The adhesive layer may contain one kind of adhesive or several kinds of adhesives. The solids content of the adhesive layer is preferably 0.01 to 100 g/m$^2$, and more preferably 0.1 to 50 g/m$^2$.

The adhesive layer also can serve the function of absorbing the vitrification solution. From such a viewpoint, it is preferable that the adhesive layer contains a water-soluble adhesive such as polyvinyl alcohol, hydroxycellulose, polyvinyl pyrrolidone and starch paste. In consideration of the adhesion strength between the support and the vitrification solution absorber, acrylic adhesives, epoxy adhesives, urethane adhesives, elastomer adhesives and cyanoacrylate adhesives are preferably used in the adhesive layer. In addition, various kinds of matting agents, surfactants, pH adjusters, etc. can be used in the adhesive layer.

Hereinbefore, the vitrification solution absorber in the present invention has been described. Hereinafter, the constitution of a device for vitrification-based cryopreservation having the vitrification solution absorber will be described. As long as the device of the present invention for vitrification-based cryopreservation has the above-described vitrification solution absorber, the constitution of the device is not particularly limited. Optionally, the vitrification solution absorber may be connected to a gripper. This option is preferable because the gripper helps smooth operation in the cryopreservation and thawing procedures.

FIG. 1 is a perspective view showing an example of the device of the present invention for cell or tissue cryopreservation by vitrification. In FIG. 1, a device for vitrification-based cryopreservation 5 is composed of a gripper 1 and a vitrification solution absorber 2. The gripper 1 is preferably made of a liquid nitrogen-resistant material. Preferable examples of such a material include various kinds of metals such as aluminum, iron, copper and stainless steel alloy, ABS resin, polypropylene resin, polyethylene resin, fluororesin, various engineering plastics and glass. The vitrification solution absorber 2 is preferably basically in the form of a strip or sheet for ease of handling.

Figure 2:
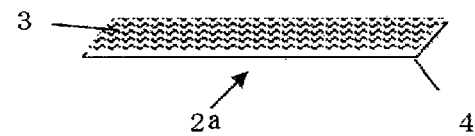
FIG. 2 is an enlarged view of the vitrification solution absorber shown in FIG. 1.

An example of the vitrification solution absorber according to the present invention is shown in FIG. 2. FIG. 2 is an enlarged view of the vitrification solution absorber 2 shown in FIG. 1. The vitrification solution absorber 2a shown in FIG. 2 has a vitrification solution absorbing layer 3 on a support 4. The vitrification solution absorber 2a shown in FIG. 2 is an embodiment in which the vitrification solution absorbing layer 3 is formed on the entire surface of the vitrification solution absorber.

The method for connecting the gripper 1 with the vitrification solution absorber 2 as shown in FIG. 1 will be described. In the case where the gripper 1 is made of resin, the vitrification solution absorber 2 can be connected to the gripper 1 in the course of molding, for example, by insert molding. Alternatively, the vitrification solution absorber 2 may be connected with an adhesive to the gripper 1 via an insertion part for the vitrification solution absorber (this part is not shown in the figure) formed in the gripper 1. Various adhesives can be used for this purpose, but preferably used are silicon adhesives and fluorine adhesives, both of which are resistant to low temperatures.

In the case where the device for cell or tissue cryopreservation by vitrification according to the present invention is used for long-term cryopreservation of cells or tissues, the body of the device shown in FIG. 1 can be covered with a cap for safety reasons, so as to be shielded from the outer environment. Liquid nitrogen is usually non-sterile, and hence a specimen frozen by direct contact with liquid nitrogen is not always guaranteed to be in an aseptic condition although the device for vitrification-based cryopreservation has been sterilized. For this reason, the vitrification solution absorber to which a cell or a tissue has been deposited is occasionally covered with a cap before freezing so as not to directly contact with liquid nitrogen in the freezing procedure. Recently, such a freezing method without direct contact with liquid nitrogen is becoming mainstream in foreign advanced countries such as the U.S. and EU. The cap is preferably made of a liquid nitrogen-resistant material such as various kinds of metals, resins, glasses and ceramics. The cap may be in any shape as long as it does not contact with the vitrification solution absorber and shields the vitrification solution absorber from the outer environment. For example, such shapes as a pencil cap and a cylindrical straw cap can be used.

Figure 3:
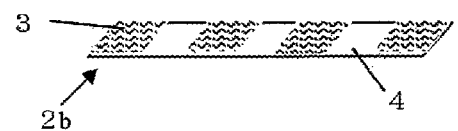
FIG. 3 is a schematic perspective view showing an example of the vitrification solution absorber of the device for cell or tissue cryopreservation by vitrification to be used in the cryopreservation of a plurality of cells or tissues per device.
Figure 4:
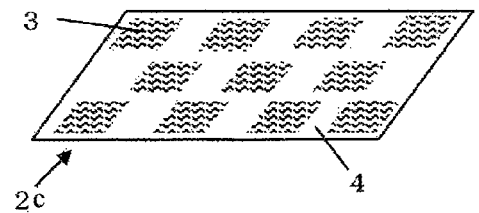
FIG. 4 is a schematic perspective view showing another example of the vitrification solution absorber of the device for cell or tissue cryopreservation by vitrification to be used in the cryopreservation of a plurality of cells or tissues per device.

Other embodiments of the vitrification solution absorber according to the present invention are shown in FIGS. 3 and 4. The vitrification solution absorber shown in FIG. 3 or 4 can be used in the device shown in FIG. 1 for cell or tissue cryopreservation by vitrification. FIG. 3 is a schematic perspective view showing a vitrification solution absorber 2b of the device for cell or tissue cryopreservation by vitrification to be used in the cryopreservation of a plurality of cells or tissues per device. FIG. 4 is a schematic perspective view showing another vitrification solution absorber 2c of the device for cell or tissue cryopreservation by vitrification to be used in the cryopreservation of a plurality of cells or tissues per device. In FIGS. 3 and 4, a vitrification solution absorbing layer 3 is divided into a plurality of parts separately arranged on a support 4.

In the case where the vitrification solution absorbing layer 3 is formed as a single piece as shown in the above-described FIG. 2, the deposition of a plurality of cells or tissues on the vitrification solution absorbing layer 3 may not be successfully performed. This is because, after the deposition of the first one of the cells or tissues, the vitrification solution-absorbing capability of the vitrification solution absorbing layer 3 is presumably reduced because the vitrification solution has already spread in the horizontal and depth directions of the vitrification solution absorbing layer. However, this risk can be reduced in the constitution where the vitrification solution absorbing layer 3 is divided into a plurality of parts separately arranged on the support 4 as shown in FIGS. 3 and 4. In this case, every single cell or tissue with a vitrification solution can be reliably deposited on a separate part of the vitrification solution absorbing layer 3. In the examples shown in FIGS. 3 and 4, a plurality of square parts constituting the vitrification solution absorbing layer 3 are arranged. The vitrification solution absorber 2b shown in FIG. 3 and the vitrification solution absorber 2c shown in FIG. 4 are examples of the vitrification solution absorber having a vitrification solution absorbing layer on part of a support.

The device of the present invention for vitrification-based cryopreservation is preferably used in the Cryotop method, for example. The use of the device of the present invention for vitrification-based cryopreservation reduces the damage to cells or tissues from the vitrification solution outside the cells or tissues in the freezing and thawing procedures, and thereby good viability of cells or tissues after the cryopreservation can be achieved.

The method for cell or tissue cryopreservation using the device of the present invention for vitrification-based cryopreservation is not particularly limited, and the cryopreservation may be performed, for example, as follows. First, a cell or tissue immersed in a vitrification solution is placed dropwise on a vitrification solution absorber. The vitrification solution surrounding the cell or tissue is then absorbed into the vitrification solution absorber. Next, the vitrification solution absorber holding the cell or tissue is immersed in liquid nitrogen etc. so that the cell or tissue will be frozen. The vitrification solution may be a vitrification solution usually used for freezing cells, such as eggs and embryos. For example, the above-mentioned aqueous solution containing a cryoprotectant, such as glycerol, ethylene glycol and DMSO (dimethyl sulfoxide), can be used.

Examples of the cell that can be cryopreserved with the device of the present invention for vitrification-based cryopreservation include reproductive cells, such as eggs, embryos and sperms, iPS cells and ES cells from mammals (for example, humans, cattle, pigs, horses, rabbits, rats, mice, etc.). Also included are culture cells such as primary culture cells, passage culture cells and cell lines. In one or more embodiments, the cell is an adhesive cell, such as a fibroblast, a cancer-derived cell such as a pancreatic cancer cell and a hepatoma cell, an epithelial cell, a vascular endothelial cell, a lymphatic endothelial cell, a neuronal cell, a chondrocyte, a tissue stem cell, an embryonic stem cell, an immune cell or the like. Examples of the tissue that can be cryopreserved with the device of the present invention include tissues formed of homologous and heterologous cells, such as ovary, skin, corneal epithelium, periodontal ligament, myocardium and cartilage. The device of the present invention for vitrification-based cryopreservation can be preferably used also when artificial tissues are cryopreserved by vitrification, let alone native cells or tissues harvested from living bodies. Examples of the artificial tissues include cultured skin formed by in vitro expansion of cells, so-called cell sheet formed in vitro, and a three-dimensional tissue model described in JP-A2012-205516.

EXAMPLES

Hereinafter, the present invention will be illustrated in more detail and specifically described by examples, but the present invention is not limited to the examples below. Various modifications and alterations can be made without departing from the technical scope of the present invention.

Example 1

On a transparent PET film which had been treated with corona discharge for adhesion improvement and had a thickness of 250 µm, a haze value of 5.5% and a total light transmittance of 91%, a urethane adhesive was applied in an amount of 10 g/m$^2$ on a dry mass basis to form an adhesive layer. Before the adhesive layer cured, a porous polytetrafluoroethylene membrane produced by stretching (refractive index: 1.35, pore size: 0.1 µm, thickness: 30 µm, porosity: 80%, surface-hydrophilized with polyvinyl alcohol) was overlaid as a porous structure on the adhesive layer and dried to form a vitrification solution absorber 2. A 40 mm²-strip of the vitrification solution absorber was joined to a gripper 1 made of ABS (acrylonitrile-butadiene-styrene) resin, to prepare a device for vitrification-based cryopreservation 5 of Example 1 in the form shown in FIG. 1.

Example 2

The device for vitrification-based cryopreservation of Example 2 was produced in the same manner as described in Example 1 except that a porous polytetrafluoroethylene membrane (refractive index: 1.35, pore size: 0.5 µm, thickness: 35 µm, porosity: 79%, surface-hydrophilized with polyvinyl alcohol) which differs in properties from the porous membrane used in Example 1 was used as a porous structure.

Example 3

The device for vitrification-based cryopreservation of Example 3 was produced in the same manner as described in Example 1 except that a porous polytetrafluoroethylene membrane (refractive index: 1.35, pore size: 1 µm, thickness: 85 µm, porosity: 80%, surface-hydrophilized with polyvinyl alcohol) which differs in properties from the porous membrane used in Example 1 was used as a porous structure.

Example 4

The device for vitrification-based cryopreservation of Example 4 was produced in the same manner as described in Example 1 except that a porous polytetrafluoroethylene membrane (refractive index: 1.35, pore size: 10 µm, thickness: 85 µm, porosity: 80%, surface-hydrophilized with polyvinyl alcohol) which differs in properties from the porous membrane used in Example 1 was used as a porous structure.

Example 5

The device for vitrification-based cryopreservation of Example 5 was produced in the same manner as described in Example 1 except that a porous polyvinylidenedifluoride membrane (refractive index: 1.42, pore size: 0.1 µm, thickness: 125 µm, porosity: 70%, surface-hydrophilized with polyvinyl alcohol) which differs in properties from the porous membrane used in Example 1 was used as a porous structure.

Example 6

The device for vitrification-based cryopreservation of Example 6 was produced in the same manner as described in Example 1 except that a porous polyvinylidenedifluoride membrane (refractive index: 1.42, pore size: 0.5 µm, thickness: 125 µm, porosity: 70%, surface-hydrophilized with polyvinyl alcohol) which differs in properties from the porous membrane used in Example 1 was used as a porous structure.

Example 7

The device for vitrification-based cryopreservation of Example 7 was produced in the same manner as described in Example 1 except that a porous polyvinylidenedifluoride membrane (refractive index: 1.42, pore size: 5 atm, thickness: 125 µm, porosity: 70%, surface-hydrophilized with polyvinyl alcohol) which differs in properties from the porous membrane used in Example 1 was used as a porous structure.

Comparative Example 1

The device for vitrification-based cryopreservation of Comparative Example 1 was produced in the same manner as described in Example 1 except that an Advantec porous cellulose acetate membrane (refractive index: 1.47, pore size: 0.5 µm, thickness: 125 µm, porosity: 68%) was used as a porous structure.

Comparative Example 2

The device for vitrification-based cryopreservation of Comparative Example 2 was produced in the same manner as described in Example 1 except that an Advantec porous mixed cellulose ester membrane made of cellulose acetate and nitrocellulose (refractive index: 1.51, pore size: 0.5 µm, thickness: 145 µm, porosity: 78%) was used as a porous structure.

Comparative Example 3

The device for vitrification-based cryopreservation of Comparative Example 3 was produced in the same manner as described in Example 1 except that a porous membrane produced by sintering polyethylene powder (refractive index: 1.51, pore size: 43 µm, thickness: 500 µm, porosity: 42%, surface-hydrophilized) was used as a porous structure.

Comparative Example 4

The device for vitrification-based cryopreservation of Comparative Example 4 was produced in the same manner as described in Example 1 except that a porous alumina membrane (pore size: 0.08 µm, thickness: 110 µm, porosity: 55%) was formed as a porous structure on a PET film. The porous alumina membrane was formed as a coating layer by applying a mixture containing 90% by mass of an alumina powder (refractive index: 1.65) and 10% by mass of a polyvinyl alcohol (PVA, refractive index: 1.52 to 1.55) binder on the PET film. The pore size of the porous alumina membrane, which cannot be determined by the bubble point test, was determined as a pore diameter at a cumulative percentage of 50%: in the pore size distribution measured by mercury intrusion porosimetry.

Comparative Example 5

The device for vitrification-based cryopreservation of Comparative Example 5 was produced in the same manner as described in Example 1 except that an Advantec filter paper No. 5C (refractive index: 1.50, basis weight: 120 g/m², density: 0.57 g/cm³), which is made of cellulose fiber, was used as a vitrification solution absorber.

Comparative Example 6

The device for vitrification-based cryopreservation of Comparative Example 6 was produced in the same manner as described in Example 1 except that a transparent PET film (thickness: 250 µm, total light transmittance: 91%, porosity:

0%), which is a clear and colorless film, was used as a vitrification solution absorber.

<Evaluation of the Visibility of Cells in the Cryopreservation Procedure>

One microliter of a vitrification solution containing a glass bead (diameter: 100 μm) as a cell mimic was deposited dropwise on the vitrification solution absorber of each of the cryopreservation devices of Examples 1 to 7 and Comparative Examples 1 to 6. The vitrification solution used was composed of modified TCM199 medium (manufactured by Sigma-Aldrich) plus 20% serum by volume, 15% DMSO by volume, 15% ethylene glycol by volume and 0.2% sucrose by volume. Whether the cell mimic deposited on each vitrification solution absorber was observable with a transmission optical microscope (manufactured by Olympus Corporation, SZH-121) was evaluated according to the criteria shown below. The results of the evaluation are shown in the column of the "Visibility of cells in cryopreservation procedure" of Table 1.

The following criteria were used for the evaluation of the visibility of cells.
A: The cell mimic is easily observable.
B: The cell mimic is observable.
C: The cell mimic is difficult or impossible to observe.

<Evaluation of the Capability of Absorbing the Vitrification Solution (1)>

One microliter of a vitrification solution containing a glass bead (diameter: 100 μm) as a cell mimic was deposited dropwise on the vitrification solution absorber of each of the cryopreservation devices of Examples 1 to 7 and Comparative Examples 1 to 6. The vitrification solution used was composed of modified TCM199 medium (manufactured by Sigma-Aldrich) plus 20% serum by volume, 15% DMSO by volume, 15% ethylene glycol by volume and 0.2% sucrose by volume. After the dropwise deposition, the absorption of the vitrification solution surrounding the cell mimic was observed with a reflected-light optical microscope (manufactured by OMRON Corporation, VC4500-S1) and evaluated according to the criteria shown below. The results of the evaluation are shown in the column of the "Capability of absorbing the vitrification solution in cryopreservation procedure (1)" of Table 1.

The following criteria were used for the evaluation of the capability of absorbing the vitrification solution.
A: The vitrification solution was fully absorbed within 10 seconds after the dropwise deposition.
B: The vitrification solution still remained at 10 seconds after the dropwise deposition, but the absorption was observed.
C: The absorption of the vitrification solution was not at all or hardly observed after the dropwise deposition.

TABLE 1

| | Capability of absorbing the vitrification solution in cryopreservation procedure (1) | Visibility of cells in cryopreservation procedure |
|---|---|---|
| Example 1 | B | A |
| Example 2 | A | A |
| Example 3 | A | A |
| Example 4 | A | A |
| Example 5 | B | B |
| Example 6 | A | B |
| Example 7 | A | B |
| Comparative Example 1 | A | C |
| Comparative Example 2 | A | C |
| Comparative Example 3 | A | C |
| Comparative Example 4 | B | C |
| Comparative Example 5 | A | C |
| Comparative Example 6 | C | A |

Example 8

The device for vitrification-based cryopreservation of Example 8 was produced in the same manner as described in Example 1 except that a porous polytetrafluoroethylene membrane (refractive index: 1.35, pore size: 0.1 μm, thickness: 35 μm, porosity: 71%, surface-hydrophilized with polyvinyl alcohol) which differs in properties from the porous membrane used in Example 1 was used as a porous structure.

Example 9

The device for vitrification-based cryopreservation of Example 9 was produced in the same manner as described in Example 1 except that a porous polytetrafluoroethylene membrane (refractive index: 1.35, pore size: 0.2 μm, thickness: 35 μm, porosity: 71%, surface-hydrophilized with polyvinyl alcohol) which differs in properties from the porous membrane used in Example 1 was used as a porous structure.

Example 10

The device for vitrification-based cryopreservation of Example 10 was produced in the same manner as described in Example 1 except that a porous polytetrafluoroethylene membrane (refractive index: 1.35, pore size: 0.5 μm, thickness: 65 μm, porosity: 79%, surface-hydrophilized with polyvinyl alcohol) which differs in properties from the porous membrane used in Example 1 was used as a porous structure.

<Evaluation of the Capability of Absorbing the Vitrification Solution (2)>

A vitrification solution containing a glass bead (diameter: 100 μm) as a cell mimic was deposited dropwise in an amount of 0.2 μL on the vitrification solution absorber of each of the above-described cryopreservation devices of Examples 3, 6 and 8 to 10, and Comparative Examples 1, 2, 5 and 6. The vitrification solution used was composed of 137 mM NaCl, 2.7 mM KCl, 0.9 mM $CaCl_2.2H_2O$, 0.5 mM $MgCl_2.6H_2O$, 1.5 mM $KH_2PO_4$, 8 mM $Na_2HPO_4$, 5.6 mM glucose, 0.3 mM sodium pyruvate, 65 μg/mL dibekacin sulfate, 1 mg/mL polyvinyl pyrrolidone, 14.8 mM L-proline, 200 mM trehalose, 30% ethylene glycol by volume, 0.5% glycerol by volume and 500 mM sucrose and supplemented with a very low concentration of phenol red as a pH indicator. After the dropwise deposition, the absorption of the vitrification solution surrounding the cell mimic was observed with a reflected-light optical microscope and evaluated according to the criteria shown below. The results of the evaluation are shown in the column of the "Capability of absorbing the vitrification solution in cryopreservation procedure (2)" of Table 2.

A: The vitrification solution around the cell was fully absorbed within 10 seconds after the dropwise deposition.

B: The vitrification solution still remained at 10 seconds after the dropwise deposition, but the absorption was observed.

C: The absorption of the vitrification solution was not at all or hardly observed after the dropwise deposition.

<Visibility of Cells in Thawing Procedure>

A mouse embryo was equilibrated in the manner shown below. The equilibrated mouse embryo with the same vitrification solution as used in the evaluation of the capability of absorbing the vitrification solution (2) was deposited dropwise on the vitrification solution absorber of each of the cryopreservation devices of Examples 3, 6 and 8 to 10 and Comparative Examples 1, 2, 5 and 6. Each device was immersed directly in liquid nitrogen for vitrification-based cryopreservation. The above-mentioned equilibration was performed as follows. A mouse embryo was firstly immersed for 10 minutes in a basal solution for vitrification which was composed of 137 mM NaCl, 2.7 mM KCl, 0.9 mM $CaCl_2.2H_2O$, 0.5 mM $MgCl_2.6H_2O$, 1.5 mM $KH_2PO_4$, 8 mM $Na_2HPO_4$, 5.6 mM glucose, 0.3 mM sodium pyruvate, 65 µg/mL dibekacin sulfate, 1 mg/mL polyvinyl pyrrolidone, 14.8 mM L-proline and 200 mM trehalose and supplemented with a very low concentration of phenol red as a pH indicator. Subsequently, the mouse embryo was taken out from the basal solution, and immersed for 5 minutes in a pretreatment solution for vitrification which was composed of 137 mM NaCl, 2.7 mM KCl, 0.9 mM $CaCl_2.2H_2O$, 0.5 mM $MgCl_2.6H_2O$, 1.5 mM $KH_2PO_4$, 8 mM $Na_2HPO_4$, 5.6 mM glucose, 0.3 mM sodium pyruvate, 65 µg/mL dibekacin sulfate, 1 mg/mL polyvinyl pyrrolidone, 14.8 mM L-proline, 200 mM trehalose, 7% ethylene by volume glycol and 0.5% glycerol by volume and supplemented with a very low concentration of phenol red as a pH indicator. The "equilibrated mouse embryo" refers to a mouse embryo taken out from the pretreatment solution for vitrification. After the cryopreservation as described above, each of the cryopreservation devices of Examples 3, 6 and 8 to 10 and Comparative Examples 1, 2, 5 and 6 on which the mouse embryo had been cryopreserved by vitrification was taken out from liquid nitrogen, and immersed in a thawing solution at 37° C. The thawing solution used was composed of 137 mM NaCl, 2.7 mM KCl, 0.9 mM $CaCl_2.2H_2O$, 0.5 mM $MgCl_2.6H_2O$, 1.5 mM $KH_2PO_4$, 8 mM $Na_2HPO_4$, 5.6 mM glucose, 0.3 mM sodium pyruvate, 65 µg/mL dibekacin sulfate, 1 mg/mL polyvinyl pyrrolidone and 300 mM sucrose and supplemented with a very low concentration of phenol red as a pH indicator. Each mouse embryo on the vitrification solution absorber immersed in the thawing solution was observed with a transmission optical microscope and the visibility of the mouse embryo was evaluated according to the criteria shown below. The results of the evaluation are shown in the column of the "Visibility of cells in thawing procedure" of Table 2.

A: The mouse embryo is easily visible.

B: The mouse embryo is visible.

C: The mouse embryo is difficult or impossible to visually confirm.

TABLE 2

|  | Capability of absorbing the vitrification solution in cryopreservation procedure (2) | Visibility of cells in cryopreservation procedure |
|---|---|---|
| Example 3 | A | B |
| Example 6 | A | A |
| Example 8 | B | A |
| Example 9 | A | A |
| Example 10 | A | A |
| Comparative Example 1 | A | C |
| Comparative Example 2 | A | C |
| Comparative Example 5 | A | C |
| Comparative Example 6 | C | A |

<Evaluation of the Viability of Mouse Embryos>
<<Harvest of Blastocyst-Stage Embryos>>

Adult female ICR mice aged from 8 to 13 weeks were allowed to naturally mate with male mice. Successful mating was confirmed from the presence of a vaginal plug. The day of confirmation of mating was designated as day 1. After about 77 hours, mouse blastocyst stage embryos were harvested from a mated female mouse by uterine flushing with KSOM/aa medium (with PVP).

<<Cryopreservation of Embryos by Vitrification>>
(Cryopreservation Devices of Examples 3 and 9)

Each mouse embryo harvested as described above was immersed in a modified phosphate buffered solution (composed of 137 mM NaCl, 2.7 mM KCl, 0.9 mM $CaCl_2.2H_2O$, 0.5 mM $MgCl_2.6H_2O$, 1.5 mM $KH_2PO_4$, 8 mM $Na_2HPO_4$, 5.6 mM glucose, 0.3 mM sodium pyruvate, 65 µg/mL dibekacin sulfate, 1 mg/mL polyvinyl pyrrolidone, 14.8 mM L-proline and 200 mM trehalose and supplemented with a very low concentration of phenol red as a pH indicator) in an environment at 15° C. for 10 minutes. Next, the mouse embryo was immersed in an equilibration solution (7% ethylene by volume glycol, 0.5% glycerol by volume and 92.5% by volume of the same modified phosphate buffered solution as described above) at 15° C. for 5 minutes. Subsequently, the mouse embryo was immersed in a vitrification solution (30% ethylene glycol by volume, 0.5% glycerol by volume, 69.5% by volume of the same modified phosphate buffered solution as described above and 0.5 M sucrose) at 4° C. for 30 seconds. After that, the mouse embryo was placed on the vitrification solution absorber of the cryopreservation device of Example 3 or 9. After microscopic observation confirmed that excess vitrification solution around each mouse embryo had been absorbed, the mouse embryo was immersed in liquid nitrogen and frozen by vitrification. After freezing, each cryopreservation device was stored in a storage vessel containing liquid nitrogen until thawing. The volume of the vitrification solution placed with the mouse embryo on the cryopreservation device was selected from the range of about 0.2 to 1 µL depending on the absorbability of the cryopreservation device.

<<Cryopreservation of Embryos by Vitrification>>
(Cryopreservation Device of Comparative Example 6)

Each mouse embryo harvested as described above was immersed in the same modified phosphate buffered solution as described above at 15° C. for 10 minutes. Next, the mouse embryo was immersed in the same equilibration solution as described above at 15° C. for 5 minutes. Subsequently, the mouse embryo was immersed in the same vitrification solution as described above at 4° C. for 30 seconds. After that, the mouse embryo was placed on the vitrification solution absorber of the cryopreservation device of Comparative Example 6. After microscopic observation confirmed that excess vitrification solution around each mouse embryo had been absorbed to a maximum extent, the mouse embryo was immersed in liquid nitrogen and frozen by vitrification. After freezing, the cryopreservation device was stored in a storage vessel containing liquid nitrogen until thawing.

In the procedure of the above-described cryopreservation of the embryos by vitrification using the cryopreservation devices of Examples 3 and 9 and Comparative Example 6, the embryo was frozen within 1 minute after the deposition on the vitrification solution absorber (the mouse embryo was frozen within 1 minute and 30 seconds after the immersion in the vitrification solution) according to the protocol recommended by KITAZATO CORPORATION.

<<Method for Thawing the Embryos>>

Each preservation device on which the mouse embryo was deposited was taken out from liquid nitrogen, and immersed in a thawing solution (a solution prepared by adding 1 M sucrose to the same modified phosphate buffered solution as described above) at 37° C. for about 1 minute. After that, the mouse embryo was recovered from the thawing solution and then immersed in a diluent (a solution prepared by adding 0.5 M sucrose to the same modified phosphate buffered solution as described above) at 37° C. The time of immersion in the diluent was about 3 minutes. Subsequently, the mouse embryo was immersed in the same modified phosphate buffered solution as described above at 37° C. for 5 minutes.

<<Evaluation of Viability>>

Each mouse embryo thawed in the above manner was transferred to KSOM/aa medium (with BSA), which is a medium for mouse embryo development, and cultured under the conditions of 5% $CO_2$, 5% $O_2$, 90% $N_2$, 37° C. and saturated humidity. The mouse embryo was observed every 4 hours after the culture started. When blastocoel formation was observed in a mouse embryo within 24 hours of culture, the mouse embryo was determined as being viable. The percentages of the number of the embryos determined as being viable in the above manner were 95.4% for the cryopreservation device of Example 3, 100% for the cryopreservation device of Example 9, and 42% for the cryopreservation device of Comparative Example 6.

The above results show that the device of the present invention for vitrification-based cryopreservation facilitates and ensures vitrification freezing of cells or tissues and subsequent thawing of the frozen cells or tissues. The device of the present invention for vitrification-based cryopreservation ensures a very high viability of cells or tissues.

INDUSTRIAL APPLICABILITY

The present invention can be used for cryopreservation of reproductive cells for embryo transfer and artificial insemination of domestic animals, such as cattle, and other animals, artificial insemination of humans, etc., and for cryopreservation of iPS cells, ES cells, commonly used culture cells, cells or tissues harvested from living bodies for the purpose of examination or implantation, in vitro cultured cells or tissues, etc.

REFERENCE SIGNS LIST

1 Gripper
2 Vitrification solution absorber
2a Vitrification solution absorber
2b Vitrification solution absorber
2c Vitrification solution absorber
3 Vitrification solution absorbing layer
4 Support
5 Device for vitrification-based cryopreservation

The invention claimed is:

1. A device for cryopreserving eggs or embryos by vitrification, the device comprising a vitrification solution absorber having a porous structure made of a material having a refractive index of 1.45 or less, wherein
after a cell or tissue immersed in a vitrification solution is placed on said vitrification solution absorber, the vitrification solution absorber absorbs excess vitrification solution surrounding the cell or tissue,
the diameter of the largest opening of the porous structure measured according to the method for bubble point testing specified in JIS K3832 is 0.75 μm or less, and
a thickness of the porous structure is 25 to 150 μm.

2. The device according to claim 1, wherein the porous structure is made of fluororesin.

3. The device according to claim 1, wherein the diameter of the largest opening measured according to the method for bubble point testing specified in JIS K3832 of the porous structure is 0.02 to 0.75 μm.

4. The device according to claim 1, wherein the diameter of the largest opening measured according to the method for bubble point testing specified in JIS K3832 of the porous structure is 0.2 to 0.75 μm.

5. The device according to claim 2, wherein the diameter of the largest opening measured according to the method for bubble point testing specified in JIS K3832 of the porous structure is 0.02 to 0.75 μm.

6. The device according to claim 2, wherein the diameter of the largest opening measured according to the method for bubble point testing specified in JIS K3832 of the porous structure is 0.2 to 0.75 μm.

* * * * *